US011612600B2

(12) United States Patent
Csonka et al.

(10) Patent No.: US 11,612,600 B2
(45) Date of Patent: *Mar. 28, 2023

(54) PHARMACEUTICAL COMPOSITION COMPRISING MACITENTAN FOR THE TREATMENT OF CHRONIC THROMBOEMBOLIC PULMONARY HYPERTENSION

(71) Applicant: ACTELION PHARMACEUTICALS LTD, Allschwil (CH)

(72) Inventors: Dénes Csonka, Allschwil (CH); Wassim Fares, Raritan, NJ (US); Hans Hoogkamer, Allschwil (CH); Koen Torfs, Beerse (BE)

(73) Assignee: Actelion Pharmaceuticals Ltd, Allschwil (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/736,434

(22) Filed: May 4, 2022

(65) Prior Publication Data

US 2022/0331319 A1 Oct. 20, 2022

Related U.S. Application Data

(63) Continuation of application No. 17/425,576, filed as application No. PCT/EP2020/051707 on Jan. 24, 2020.

(30) Foreign Application Priority Data

Jan. 25, 2019 (WO) .............. PCT/EP2019/051874
Apr. 18, 2019 (WO) .............. PCT/EP2019/060152
Jun. 21, 2019 (WO) .............. PCT/EP2019/066495
Jun. 27, 2019 (WO) .............. PCT/EP2019/067187

(51) Int. Cl.
*A61K 31/506* (2006.01)
*A61K 45/06* (2006.01)
*A61P 9/12* (2006.01)

(52) U.S. Cl.
CPC .............. *A61K 31/506* (2013.01); *A61K 45/06* (2013.01); *A61P 9/12* (2018.01)

(58) Field of Classification Search
CPC .......... A61K 31/506; A61K 45/06; A61P 9/12
USPC ....................................................... 514/274
See application file for complete search history.

(56) References Cited

U.S. PATENT DOCUMENTS

| | | | |
|---|---|---|---|
| 7,094,781 B2 | 8/2006 | Bolli et al. | |
| 7,285,549 B2 | 10/2007 | Bolli et al. | |
| 8,268,847 B2 | 9/2012 | Clozel | |
| 8,324,232 B2 | 12/2012 | Bolli et al. | |
| 8,367,685 B2 | 2/2013 | Adesuyi et al. | |
| 8,809,334 B2 | 8/2014 | Clozel | |
| 9,173,881 B2 | 11/2015 | Clozel | |
| 9,265,762 B2 | 2/2016 | Adesuyi et al. | |
| 9,597,331 B2 | 3/2017 | Clozel | |
| 10,117,870 B2 | 11/2018 | Adesuyi et al. | |
| 10,919,881 B2 | 2/2021 | Bolli et al. | |
| 10,946,015 B2 | 3/2021 | Lithgow et al. | |
| 11,174,247 B2 | 11/2021 | Bellet et al. | |
| 11,234,980 B2 * | 2/2022 | Csonka .................. | A61P 11/00 |
| 2004/0077670 A1 | 4/2004 | Bolli et al. | |
| 2006/0178365 A1 | 8/2006 | Bolli et al. | |
| 2008/0233188 A1 | 9/2008 | Adesuyi et al. | |
| 2009/0318459 A1 | 12/2009 | Clozel | |
| 2010/0004274 A1 | 1/2010 | Adesuyi et al. | |
| 2011/0136818 A1 | 6/2011 | Clozel | |
| 2013/0005734 A1 | 1/2013 | Clozel | |

(Continued)

FOREIGN PATENT DOCUMENTS

WO 2002/053557 7/2002
WO 2007/031933 A2 3/2007
(Continued)

OTHER PUBLICATIONS

Nashat et al, Europian Respiratory Journal Sep. 1, 2018 European Respiratory society NLD, v52 Supplement 62, Sep. 1, 2018. (Year: 2018).*
"PORtopulmonary Hypertension Treatment with maCitentan—a randomized Clinical Trial (PORTICO)," History of Changes for Study: NCT02382016, ClinialTrials.gov Archive, Dec. 19, 2018, pp. 1-20.
Adesuyi et al., U.S. Appl. No. 17/116,983, entitled "Stable Pharmaceutical Compositions Comprising a Pyrimidine-Sulfamide", filed on Dec. 9, 2020.
Ahn et al: "Pharmacokinetic-Pharmacodynamic Relationships of Macitentan, a New Endothelin Receptor Antagonist, After Multiple Dosing in Healthy Korean Subjects", American Journal of Cardiovascular Drugs, vol. 14, No. 5, Oct. 2014 , pp. 377-385.

(Continued)

*Primary Examiner* — Yevgeny Valenrod
(74) *Attorney, Agent, or Firm* — BakerHostetler

(57) ABSTRACT

The present invention relates to high doses of macitentan (INN), i.e. propylsulfamic acid [5-(4-bromo-phenyl)-6-[2-(5-bromo-pyrimidin-2-yloxy)-ethoxy]-pyrimidin-4-yl]-amide or pharmaceutically acceptable salts, solvates, hydrates or morphological forms thereof, or of aprocitentan, for use in the treatment and/or prevention of chronic thromboembolic pulmonary hypertension (CTEPH). Moreover, the present invention relates to the use of high doses of macitentan or of aprocitentan for the manufacture of a medicament for the treatment and/or prevention of CTEPH, as well as to a method for the treatment and/or prevention of CTEPH comprising administering high doses of macitentan or of aprocitentan to a patient. Further, the present invention relates to a dosage regimen for the treatment and/or prevention of CTEPH as well as to a combination of macitentan, or of aprocitentan, with one or more phosphodiesterase type 5 (PDE5) inhibitors, prostacyclin analogues, prostacyclin receptor agonists or soluble guanylate cyclase stimulators. Moreover, the present invention relates to a pharmaceutical composition for the treatment of CTEPH comprising a high dose of macitentan or of aprocitentan.

20 Claims, 1 Drawing Sheet

(56) References Cited

U.S. PATENT DOCUMENTS

| | | |
|---|---|---|
| 2013/0210830 A9 | 1/2013 | Clozel |
| 2013/0190336 A1 | 7/2013 | Adesuyi et al. |
| 2014/0148460 A1 | 5/2014 | Clozel |
| 2014/0329824 A1 | 11/2014 | Clozel |
| 2016/0022678 A1 | 1/2016 | Clozel |
| 2016/0136163 A1 | 5/2016 | Adesuyi et al. |
| 2018/0147205 A1 | 5/2018 | Clozel |
| 2018/0263980 A1 | 9/2018 | Lithgow et al. |
| 2019/0083494 A1 | 3/2019 | Clozel |
| 2019/0321328 A1 | 10/2019 | Behan et al. |
| 2020/0002317 A1 | 1/2020 | Bolli et al. |
| 2020/0038401 A1 | 2/2020 | Clozel |
| 2020/0061061 A1 | 2/2020 | Bellet et al. |
| 2020/0352944 A1 | 11/2020 | Clozel |
| 2021/0177849 A1 | 6/2021 | Clozel |
| 2021/0186966 A1 | 6/2021 | Adesuyi et al. |
| 2021/0196715 A1 | 7/2021 | Fares et al. |
| 2021/0206750 A1 | 7/2021 | Bolli et al. |
| 2022/0096474 A1* | 3/2022 | Csonka ............ A61P 9/12 |
| 2022/0096476 A1* | 3/2022 | Csonka ............ A61P 9/12 |

FOREIGN PATENT DOCUMENTS

| | | |
|---|---|---|
| WO | 2008/026156 A2 | 3/2008 |
| WO | 2009/024906 A1 | 2/2009 |
| WO | 2010/018549 A2 | 2/2010 |
| WO | 2018/089804 A1 | 5/2018 |
| WO | 2018/153513 A1 | 8/2018 |
| WO | 2018/153925 A1 | 8/2018 |
| WO | 2020/128017 A1 | 6/2020 |
| WO | 2020/152308 A1 | 7/2020 |
| WO | 2020/201479 A1 | 10/2020 |
| WO | 2021/105164 A1 | 6/2021 |

OTHER PUBLICATIONS

Anonymous: "Opsumit 10 mg film-coated tablets", EMA, Package leaflet: information for the user, Jan. 13, 2017, pp. 1-6, XP055679353, Retrieved from the Internet: URL:https://www.actelion.com/documents/enrebranded/our-products/opsumit-pil.pdf [retrieved on Mar. 24, 2020].

Bedan et al.: A Focus on Macitentan in the Treatment of Pulmonary Arterial Hypertension 11, Basic & Clinical Pharmacology & Toxicology, vol. 123, No. 2, Jun. 5, 2018 (Jun. 5, 2018), XP055679362, pp. 103-113.

Benza et al., "An evaluation of long-term survival from time of diagnosis in pulmonary arterial hypertension from the REVEAL Registry", Chest, 2012, 142(2), 448-456.

Benza et al., "The REVEAL Registry Risk Score Calculator in Patients Newly Diagnosed With Pulmonary Arterial Hypertension", Chest, 2012, 141(2), 354-362.

Bruderer et al., "Absorption, distribution, metabolism, and excretion of macitentan, a dual endothelin receptor antagonist, in humans", Xenobiotica, 2012, 42(9), 901-910.

Clozel, U.S. Appl. No. 17/185,238, entitled "Therapeutic Compositions", filed Feb. 25, 2021.

Csonka et al., Pharmaceutical Composition Comprising Macitentan for the Treatment of Chronic Thromboembolic Pulmonary Hypertension, Jul. 23, 2021, U.S. Appl. No. 17/425,576.

Csonka et al., Pharmaceutical Composition For The Treatment Of Pulmonary Arterial Hypertension, Oct. 29, 2021, U.S. Appl. No. 17/515,132.

Delcroix, et al., "Long-term outcome of patients with chronic thromboembolic pulmonary hypertension: results from an international prospective registry," Circulation AHA, vol. 133, Issue 9, Mar. 1, 2016, 2016, pp. 859-871.

Dorfmüller, et al., "Microvascular disease in chronic thromboembolic pulmonary hypertension: a role for pulmonary veins and systemic vasculature," Eur. Respir. J, vol. 44, 2014, pp. 1275-1288.

Edward et al., "An Update on the Management of Chronic Thromboembolic Pulmonary Hypertension," Current Problems in Cardiology, vol. 42, No. 1, Nov. 14, 2016, pp. 7-38.

European Medicines Agency, European Public Assessment Report for Opsumit, Procedure No. EMEA/H/C/002697/0000 (2013) at 20 "EMA Assessment Report".

Fedullo, et al., "Chronic thromboembolic pulmonary hypertension," Am. J. Respir. Crit. Care Med, vol. 183, Feb. 17, 2011, pp. 1605-1613.

Galie et al., "ESC/ERS Guidelines", European Heart Journal, 2016, 37, 67-119.

Graham et al., "2017 ERS/ATS standards for single-breath carbon monoxide uptake in the lung", Eur. Respir. J., 2017, 49, 31 pages.

Heli, B., et al., "Portopulmonary hypertension—novel management of a rare complication of cirrhosis in children," Hepatology, Wiley Interscience, US, vol. 68, No. Supplement, Nov. 9, 2018, p. 767A-768A.

Hullin,"New compounds for the treatment of pulmonary hypertension", Cardiovascular Medicine, vol. 21, Issue 7-8, 2018, pp. 195-199.

Iglarz et al., "Comparison of Pharmacological Activity of Macitentan and Bosentan in Preclinical Models of Systemic and Pulmonary Hypertension", Life Sci., 2014, 118, 333-339.

Iglarz et al., "Pharmacology of macitentan, an orally active tissue-targeting dual endothelin receptor antagonist", J. Pharmacol. Exp. Ther., 2008, 327(3), 736-745.

Jansa et al. Am. J. Cardiovasc. Drugs, 2018, vol. 18, pp. 1-11 (Year: 2018).

Jensen, et al., "Pulmonary hypertensive medical therapy in chronic thromboembolic pulmonary hypertension before pulmonary thromboendarterectomy," Circulation, vol. 120, Sep. 14, 2009, pp. 1248-1254.

Juli En Vionnet et al., "Management of Severe Portopulmonary Hypertension With Dual Oral Therapy Before Liver Transplantation," Transplantation, vol. 102, No. 5, May 1, 2018, p. e194.

Keating (Am J. Cardiovasc. Drugs, 2016, vol. 16, pp. 453-460) (Year: 2016).

Kenneth, et al., "Pulmonary vascular lesions occurring in patients with chronic major vessel thromboembolic pulmonary hypertension," Chest, vol. 103, Mar. 3, 1993, pp. 685-692.

Kholdani, et al.,"Macitentan for the treatment of pulmonary arterial hypertension", Vascular Health and Risk Management, vol. 10, Nov. 25, 2014, pp. 665-673.

Kim, et al., "Chronic thromboembolic pulmonary hypertension," ERJ Express, Dec. 13, 2018, pp. 1-10.

Kim, et al., "Chronic thromboembolic pulmonary hypertension," Journal of the American College of Cardiology, vol. 62, No. 25, 2013, pp. D92-D99.

Kramm, et al., "Inhaled iloprost in patients with chronic thromboembolic pulmonary hypertension: effects before and after pulmonary thromboendarterectomy," Ann. Thorac. Surg, vol. 76, 2003, pp. 711-718.

Krug, et al., "Acute improved hemodynamics following inhaled iloprost in chronic thromboembolic pulmonary hypertension," Respiration, vol. 76, Sep. 5, 2007, pp. 154-159.

Kunita-Takanezawa et al., "Novel Dual Endothelin Receptor Antagonist Macitentan Reverses Severe Pulmonary Arterial Hypertension in Rats", J Cardiovasc Pharmacol , 2014, 64(5), 473-480.

Lang, et al., "Risk factors and basic mechanisms of chronic thromboembolic pulmonary hypertension: a current understanding," European Respiratory Journal, vol. 41, Jun. 14, 2012, pp. 462-468.

M Krowka., "Treatment of portopulmonary hypertension with macitentan in patients with cirrhosis," Gastroenterology and Hepatology, Feb. 2, 2019, pp. 108-110.

M. Krowka et al., "Efficacy and Safety of Macitentan in Patients with Portopulmonary Hypertension: The Randomized, Placebo Controlled Portico Trial," Hepatology, Nov. 9, 2018, pp. 70A-71A.

M. Krowka et al., "Macitentan Improves Risk Categorization for Liver Transplant Mortality in Patients With Portopulmonary Hypertension: A Portico Study Post Hoc Analysis," Liver transplantation, Mar. 9, 2020, pp. 1-6.

Macitentan, "Assessment Report: Opsumit," European Medicines Agency: Science Medicines Health, Procedure No. EMEA/H/C/002697/0000, Oct. 24, 2013, p. 105.

(56) References Cited

OTHER PUBLICATIONS

Madani, et al., "Pulmonary endarterectomy. Patient selection, technical challenges, and outcomes,". Ann. Am. Thorac. Soc, vol. 13, (SuppL 3), Jul. 2016, pp S240-S247.
Mehta et al. Chest, 2017, vol. 151, No. 1, pp. 106-118 (Year: 2017).
Monaco etal. Drug Design, Development and Therapy, May 18, 2016, vol. 10, pp. 1675-1682 (Year: 2016).
Morrell et al., "Genetics and genomics of pulmonary arterial hypertension", Eur. Respir. J., Jan. 2019, 53(1):1801899.
Nagaya, et al., "Prostacyclin therapy before pulmonary thromboendarterectomy in patients with chronic thromboembolic pulmonary hypertension," Chest, vol. 2, issue 123, Feb. 2003, pp. 338-343.
Nashat et al., "Clinical efficacy of Macitentan in patients with Pulmonary Arterial Hypertension and Chronic Thromboembolic Pulmonary Hypertension," Database accession No. EB-626626306 abstract & Europe Respiratory Journal Sep. 1, 2018 European Respiratory Society NLD, vol. 52, No. Supplement 62, Sep. 1, 2018.
Ogo, T., "Balloon pulmonary angioplasty for inoperable chronic thromboembolic pulmonary hypertension," Current Opinion, vol. 21, No. 5, Sep. 2015, pp. 425-431.
Opsumit (Registered) (macitentan) Product Label (2013) (Accessed from https://www.accessdata.fda.gov/drugsatfda_docs/label/2013/204410s000lbl.pdf on Apr. 16, 2021) (Year: 2013).
Pepka-Zaba, et al., "Chronic thromboembolic pulmonary hypertension (CTEPH): results from an international prospective registry," Circulation, vol. 124, Oct. 3, 2011, pp. 1973-1981.
Sidharta et al..,"Macitentan: entry-into-humans study with a new endothelin receptor antagonist," European Journal of Clinical Pharmacology, vol. 67, No. 10, May 4, 2011, pp. 977-984.
Sidharta et al.: "Safety, tolerability, pharmacokinetics, and pharmacodynamics of macitentan, an endothelin receptor antagonist, in an ascending multiple-dose study in healthy subjects: The Journal of Clinical Pharmacology", Journal of Clinical Pharmacology., vol. 53, No. 11, Aug. 2013 (Aug. 2013), XP055678913, pp. 1131-1138.
Simonneau et al., "Haemodynamic definitions and updated clinical classification of pulmonary hypertension", Eur. Respir. J., Jan. 2019, 53(1):1801913.
Simonneau et al., "Macitentan for inoperable chronic thromboembolic pulmonary hypertension (CTEPH): results from the randomised controlled MERIT study," Pulmonary Circulation and Pulmonary Vascular Disease Sep. 1, 2017, p. 0A1984.
Simonneau, et al., "The pathophysiology of chronic thromboembolic pulmonary hypertension," Eur. Respir. Rev, 2017, 26, 160112.
Suntharalingam, et al., "Long-term use of sildenafil in inoperable chronic thromboembolic pulmonary hypertension," Chest, vol. 134, Aug. 2, 2008, pp. 229-236.
T. Ueno et al., "Pulmonary Arterial Pressure Management Based on Oral Medicine for Pediatric Living Donor Liver Transplant With Portopulmonary Hypertension," Transplantation Proceedings, vol. 50, No. 9, Nov. 1, 2018, pp. 2614-2618.
Torbicki, "Macitentan for treatment of CTEPH: why MERIT merits attention," The Lancet. Respiratory Medicine, vol. 5, No. 10, Oct. 1, 2017, pp. 762-763.
U.S. patent application filed Oct. 4, 2021, by Loïc Perchenet, entitled "Macitentan for Use in Treating Portopulmonary Hypertension", U.S. Appl. No. 17/601,123.
Yokoyama et al., "Tolerability, Safety, Pharmacokinetics, and Pharmacodynamics of Macitentan, a New Endothelin Receptor Antagonist, in Healthy Japanese Male Subjects", Rinsho Yakuri/ Japanese Journal of Clinical Pharmacology and Therapeutics, 2016, 47, 143-150.
Angoletti et al., "Endothelin inhibitors lower pulmonary vascular resistance and improve functional capacity in patients with Fontan circulation", The Journal of Thoracic and Cardiovascular Surgery, vol. 153, No. 6, Feb. 10, 2017, pp. 1468-1475.
Apostolopoulou et al., "Bosentan induces clinical, exercise and hemodynamic improvement in a pre-transplant patient with plastic bronchitis after Fontan operation," J. Heart Lung Transplant, Aug. 2005, vol. 24, No. 8, pp. 1174-1176.
Demetriades et al.,"The use of Macitentan in Fontan circulation: a case report", BMC Cardiovascular Disorders, vol. 17, No. 1, May 22, 2017, pp. 1-3.
Fontan et al., "Outcome after a"perfect" Fontan operation," Circulation, vol. 81, Issue 5, 1990, pp. 1520-1536.
Gabbay et al., "Review of bosentan in the management of pulmonary arterial hypertension," Vascular health and risk management, Dec. 2007, vol. 3, Issue 6, pp. 887-900.
Galie et al., "2015 ESC/ERS guidelines for the diagnosis and treatment of pulmonary hypertension: the joint task force for the diagnosis and treatment of pulmonary hypertension of the European Society of Cardiology (ESC) and the European Respiratory Society (ERS): endorsed by: Association for European Paediatric and Congenital Cardiology KAEPC), International Society for Heart and Lung Transplantation (ISHLT)," European heart journal, Jan. 1, 2016, vol. 37, Issue 1, pp. 67-119.
Gewillig, "The fontan circulation", Heart, Jun. 1, 2005, vol. 91, Issue 6, pp. 839-846.
Ghofrani et al., "Macitentan for the treatment of inoperable chronic thromboembolic pulmonary hypertension (MERIT-1): results from the multicentre, phase 2, randomised, double-blind, placebo-controlled study", Lancet Respir. Med., vol. 5, Oct. 2017, pp. 785-794.
Griffiths et al., "Evaluating failing Fontans for heart transplantation: predictors of death," The Annals of thoracic surgery, Aug. 1, 2009, vol. 88, Issue 2, pp. 558-564.
Hebert et al., "The effect of bosentan on exercise capacity in Fontan patients; rationale and design for the TEMPO Study", BMC Cardiovasc. Disord, 2013, vol. 13, Article No. 36, pp. 1-7.
Hosein et al., "Factors influencing early and late outcome following the Fontan procedure in the current era. The 'Two Commandments'?" European journal of cardio-thoracic surgery, Mar. 1, 2007, vol. 31, Issue 3, 344-353.
Kirklin et al., "Therapeutic use of right atrial pressures early after the Fontan operation," European journal of cardio-thoracic surgery, Jan. 1, 1990, vol. 4, Issue 1, pp. 2-7.
Kovacs et al., "Pulmonary arterial pressure during rest and exercise in healthy subjects: a systematic review," European Respiratory Journal, Oct. 1, 2009, vol. 34, Issue 4, pp. 888-894.
Malhotra et al., "Cardiopulmonary exercise testing in heart failure", JACC: Heart Failure, 2016, vol. 4, No. 8, pp. 607-616.
Miyaji et al., "Combined therapy with inhaled nitric oxide and intravenous epoprostenol (prostacyclin) for critical pulmonary perfusion after the Fontan procedure," The Journal of Thoracic and Cardiovascular Surgery, Feb. 1, 2003, vol. 125, Issue 2, pp. 437-439.
Tabitha "Macitentan use as serial therapy in failing fontan physiology", Journal Of The American College of Cardiology, vol. 69, No. 11, Dec. 31, 2017, p. 632.
Takahashi et al., "Effect of beraprost sodium on pulmonaryvascular resistance in candidates for a Fontan procedure: A preliminarystudy," Pediatrics international, Dec. 2003, vol. 45, Issue 6, pp. 671-675.
Valerio et al., "Bosentan in the treatment of pulmonary arterial hypertension with the focus on the mildly symptomatic patient," Vascular health and risk management, 2009, vol. 5, pp. 607-619.
Van Der Ven et al., "State of the art of the Fontan strategy for treatment of univentricular heart disease," F1000Research, 2018, vol. 7, pp. 1-14.

* cited by examiner

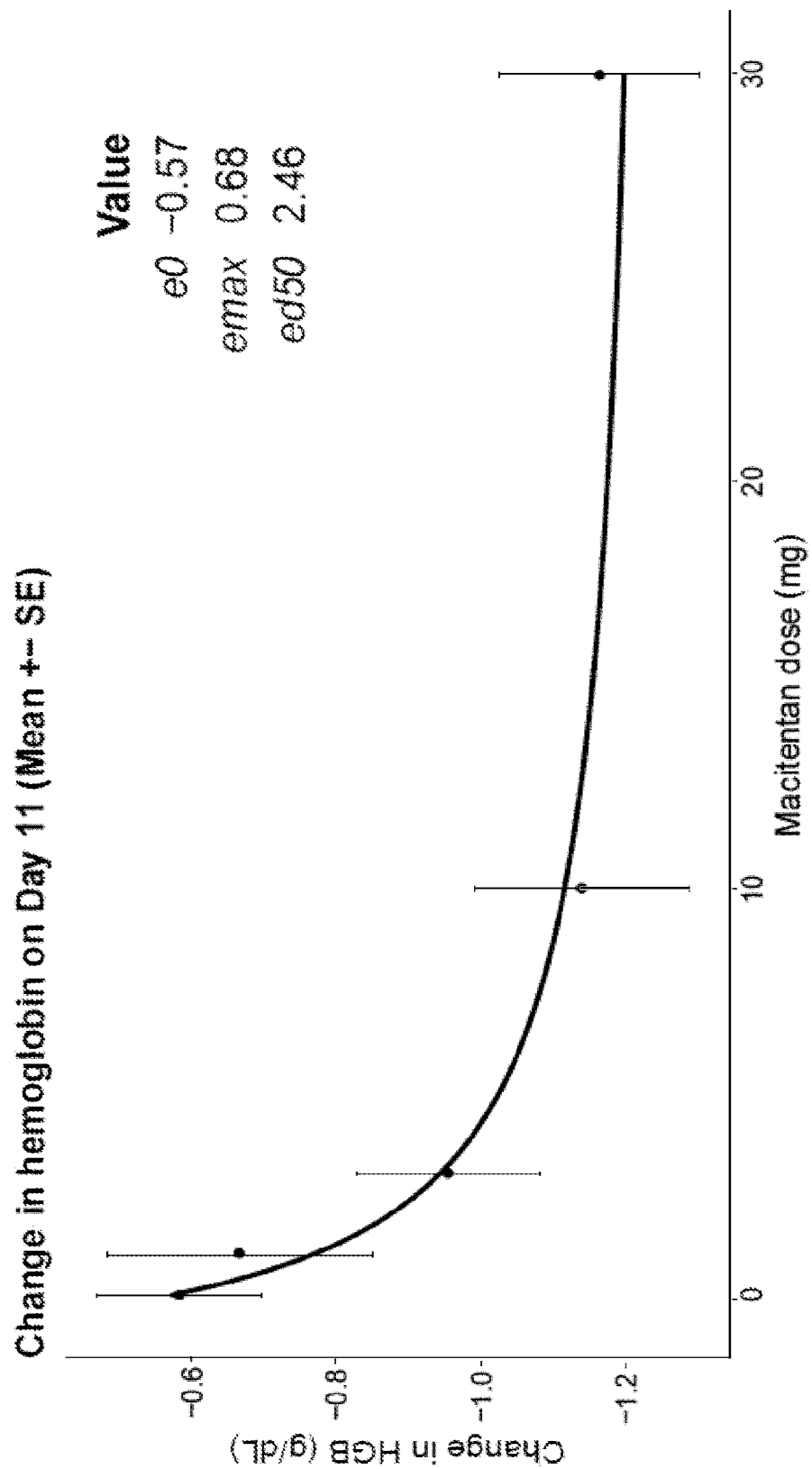

PHARMACEUTICAL COMPOSITION COMPRISING MACITENTAN FOR THE TREATMENT OF CHRONIC THROMBOEMBOLIC PULMONARY HYPERTENSION

CROSS-REFERENCE TO RELATED APPLICATIONS

This application is a continuation of U.S. patent application Ser. No. 17/425,576, filed Jul. 23, 2021, which is a U.S. national stage of International Patent Application No. PCT/EP2020/051707, filed Jan. 24, 2020, which claims the benefit of International Patent Application No. PCT/EP2019/051874, filed Jan. 25, 2019; International Patent Application No. PCT/EP2019/060152, filed Apr. 18, 2019; International Patent Application No. PCT/EP2019/066495, filed Jun. 21, 2019 and International Patent Application No. PCT/EP2019/067187, filed Jun. 27, 2019, the contents of which are incorporated herein by reference.

FIELD OF THE INVENTION

The present invention relates to high doses of macitentan (INN), i.e. propylsulfamic acid [5-(4-bromo-phenyl)-6-[2-(5-bromo-pyrimidin-2-yloxy)-ethoxy]-pyrimidin-4-yl]-amide or pharmaceutically acceptable salts, solvates, hydrates or morphological forms thereof, or of aprocitentan, for use in the treatment and/or prevention of chronic thromboembolic pulmonary hypertension (CTEPH). Moreover, the present invention relates to the use of high doses of macitentan or of aprocitentan for the manufacture of a medicament for the treatment and/or prevention of CTEPH, as well as to a method for the treatment and/or prevention of CTEPH comprising administering high doses of macitentan or of aprocitentan to a patient. Further, the present invention relates to a dosage regimen for the treatment and/or prevention of CTEPH as well as to a combination of macitentan, or of aprocitentan, with one or more phosphodiesterase type 5 (PDE5) inhibitors, prostacyclin analogues, prostacyclin receptor agonists or soluble guanylate cyclase stimulators. Moreover, the present invention relates to a pharmaceutical composition for the treatment of CTEPH comprising a high dose of macitentan or of aprocitentan.

BACKGROUND

Pulmonary hypertension (PH) was reported for the first time in 1891 when the autopsy of a patient with sudden death revealed right ventricular hypertrophy and pulmonary artery sclerosis without any apparent cause. Chronic thromboembolic pulmonary hypertension (CTEPH) is a subgroup of PH. PH is clinically classified into five groups according to the World Health Organization (WHO) classification: pulmonary arterial hypertension (PAH) (group 1), PH related to left heart disease (group 2), PH due to lung disease and/or hypoxia (group 3), chronic thromboembolic PH and other pulmonary artery obstructions (group 4), and PH with unclear and/or multifactorial mechanisms (group 5) (Hullin, *Cardiovascular Medicine* (2018), 21(7-8), 195-199; Simonneau et al., Haemodynamic definitions and updated clinical classification of pulmonary hypertension. *Eur. Respir. J.* (2018), Dec. 13. pii: 1801913; Kim et al., Chronic thromboembolic pulmonary hypertension, *Eur. Respir. J.* (2018), in press (https://doi.org/10.1183/13993003.01915-2018)].

The present invention focuses on CTEPH, which is a type of pulmonary hypertension resulting from fibrotic transformation of pulmonary artery clots causing chronic obstruction in macroscopic pulmonary arteries and associated vascular remodeling in the microvasculature. CTEPH is haemodynamically characterised by the presence of a mean pulmonary artery pressure (PAP)>20 mm Hg, a pulmonary artery wedge pressure (PAWP)≤15 mm Hg and a PVR of ≥3 Wood units, alternatively >2 Wood units, all measured at rest. There are unresolved chronic blood clots in the lungs that lead to pulmonary artery occlusions and/or stenosis.

Chronic thromboembolic pulmonary hypertension (CTEPH) is a complication of pulmonary embolism and a major cause of chronic PH leading to right heart failure and death [Kim et al., Chronic thromboembolic pulmonary hypertension. *Eur. Respir. J.* (2018), in press (https://doi.org/10.1183/13993003.01915-2018)]. Lung ventilation/perfusion scintigraphy is the screening test of choice; a normal scan rules out CTEPH. In the case of an abnormal perfusion scan, a high-quality pulmonary angiogram is necessary to confirm and define the pulmonary vascular involvement and prior to making a treatment decision. PH is confirmed with right heart catheterisation, which is also necessary for treatment determination. In addition to chronic anticoagulation therapy, each patient with CTEPH should receive treatment assessment starting with evaluation for pulmonary endarterectomy, which is the guideline recommended treatment. For technically inoperable cases, PH-targeted medical therapy is recommended (currently riociguat based on the CHEST studies), and balloon pulmonary angioplasty should be considered at a centre experienced with this challenging but potentially effective and complementary intervention.

SUMMARY OF THE INVENTION

It is an object of the present invention to provide a medication and/or treatment regimen for chronic thromboembolic pulmonary hypertension (CTEPH). It is a further object of the present invention to provide a combination medication and/or treatment for CTEPH. Moreover, it is an object of the present invention to provide the medication and/or treatment regimen or combination medication to specific patient populations with CTEPH. Moreover, it is an object of the present invention to provide a pharmaceutical composition for use in the treatment of CTEPH.

BRIEF DESCRIPTION OF THE FIGURES

FIG. 1 is a dose-response curve showing the change in hemoglobin (HGB) in function of the dose of macitentan administered to a human.

DETAILED DESCRIPTION

The present inventors have recognized that, despite fears of clinically relevant hemoglobin decreases, blood pressure decreases and/or edema or fluid retention increases, it is possible, safe and effective to treat CTEPH patients with high doses of macitentan. In particular, it is possible to decrease the progress of the disease, or even to improve the status of the disease.

In the present invention, macitentan is defined as propylsulfamic acid [5-(4-bromo-phenyl)-6-[2-(5-bromo-pyrimidin-2-yloxy)-ethoxy]-pyrimidin-4-yl]-amide, i.e. a compound of formula (I)

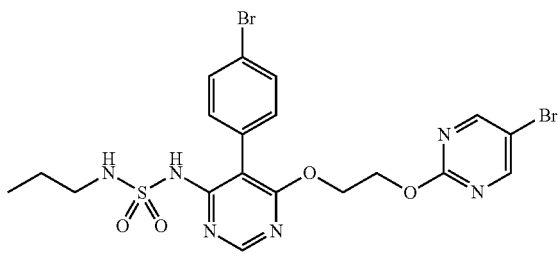

(I)

or a pharmaceutically acceptable salt, solvate, hydrate or morphological form thereof.

Macitentan is an endothelin receptor antagonist (ERA) that acts as an antagonist of two endothelin (ET) receptor subtypes, $ET_A$ and $ET_B$ (Kholdani et al., Macitentan for the treatment of pulmonary arterial hypertension. *Vasc. Health Risk Manag.* (2014), 10, 665-673). Its half-life in humans is about 16 hours and steady state is reached by the third day of administration (Bruderer et al., Absorption, distribution, metabolism, and excretion of macitentan, a dual endothelin receptor antagonist, in humans. *Xenobiotica* (2012), 42(9), 901-910). It is absorbed slowly into the plasma (Sidharta et al., Macitentan: entry-into-humans study with a new endothelin receptor antagonist. *Eur. J. Clin. Pharmacol.* (2011), 67, 977-984). Macitentan dealkylates into the active metabolite ACT-132577, which reaches its peak plasma concentration about 30 hours after the first dose is administered, and it has a half-life of approximately 48 hours. Although ACT-132577 has a lower affinity for the ET receptors than its parent compound (Iglarz et al., Pharmacology of macitentan, an orally active tissue-targeting dual endothelin receptor antagonist. *J. Pharmacol. Exp. Ther.* (2008), 327(3), 736-745), it maintains higher plasma concentrations than macitentan. Both compounds can be excreted from the body through the urine or feces.

It has previously been reported that the maximal or near-maximal effect of macitentan in rats is 10 mg/kg. (European Medicines Agency, European Public Assessment Report for Opsumit, Procedure No. EMEA/H/C/002697/0000 (2013) at 20 ("EMA Assessment Report")). It has also previously been reported that the maximal effective dose of macitentan in rats is 30 mg/kg (Id.; e.g., Iglarz et al., Comparison of Pharmacological Activity of Macitentan and Bosentan in Preclinical Models of Systemic and Pulmonary Hypertension. *Life Sci.* (2014), 118, 333-339; see also Kunita-Takanezawa et al., Novel Dual Endothelin Receptor Antagonist Macitentan Reverses Severe Pulmonary Arterial Hypertension in Rats. *J. Cardiovasc. Pharmacol.* (2014), 64(5), 473-480).

In a multiple-ascending dose study evaluating 1 mg, 3 mg, 10 mg, and 30 mg dosages of macitentan in healthy human subjects, plasma ET-1 concentrations at steady-state showed a dose-dependent increase, with no further increase beyond the 10 mg oral dose, indicating blockade at this dosage. (Id. at 40). The evaluators concluded that the 10 mg dose appeared to be close to the plateau of the pharmacological effect. (Id. at 48). The European Medicines Agency and the U.S. Food and Drug Administration have approved the 10 mg daily oral dosage of macitentan for the treatment of patients with pulmonary arterial hypertension. (EMA, Summary of Product Characteristics for Opsumit (Oct. 29, 2019) at 2; FDA, Prescribing Information for Opsumit (April 2019) at 1).

In the following, several aspects of the invention will be explained.

One aspect of the present invention relates to macitentan for use in the treatment and/or prevention of chronic thromboembolic pulmonary hypertension (CTEPH) in human, wherein the dosage of macitentan is from 20 mg per day to 300 mg per day, for example, from 20 mg per day to 250 mg per day, preferably from 25 mg per day to 200 mg per day and more preferably from 25 mg per day to 150 mg per day. Further dosage ranges are 30 mg per day to 300 mg per day, for example, 30 mg per day to 250 mg per day, 30 mg per day to 200 mg per day or 35 mg per day to 180 mg per day.

According to a more preferred aspect, the dosage is applied once a day.

In the present invention, CTEPH is defined as chronic thromboembolic pulmonary hypertension in human.

CTEPH is characterized by
- a mean pulmonary artery pressure (mPAP)>20 mm Hg,
- a pulmonary artery wedge pressure (PAWP)≤15 mm Hg,
- a pulmonary vascular resistance (PVR)≥3 Wood units, alternatively >2 Wood units, and
- unresolved chronic blood clots in the lungs that lead to pulmonary artery occlusions and/or stenosis.

Therein, each Wood unit is 80 dynes·sec·cm$^{-5}$.

CTEPH is characterised pathologically by organized thromboembolic material and by altered vascular remodeling initiated or potentiated by a combination of defective angiogenesis, impaired fibrinolysis and endothelial dysfunction [Kim et al., Chronic thromboembolic pulmonary Hypertension. *Eur. Respir. J.* (2018), 1-10; Lang et al., Risk factors and basic mechanisms of chronic thromboembolic pulmonary hypertension: a current understanding. *Eur. Respir. J.* (2013), 41, 462-468; Moser and Bloor, Pulmonary vascular lesions occurring in patients with chronic major vessel thromboembolic pulmonary hypertension. *CHEST* (1993), 103, 685-692; Dorfmüller et al., Microvascular disease in chronic thromboembolic pulmonary hypertension: a role for pulmonary veins and systemic vasculature. *Eur. Respir. J.* (2014), 44, 1275-1288]. These changes lead to PH and ultimately right ventricular failure [Kim et al., Chronic thromboembolic pulmonary hypertension. *J. Am. Coll. Cardiol.* (2013), 62, D92-D99; Fedullo et al., Chronic thromboembolic pulmonary hypertension. *Am. J. Respir. Crit. Care Med.* (2011), 183, 1605-1613]. The precise pathogenesis of CTEPH remains unclear but appears to be incited by acute pulmonary embolism [Simonneau et al., The pathophysiology of chronic thromboembolic pulmonary hypertension. *Eur. Respir. Rev.* (2017), 26, 160112] although a history of acute pulmonary embolism is not present in a significant proportion of CTEPH patients.

A Wood Unit is the measure of a simplified system for measuring pulmonary vascular resistance (PVR) that uses increments of pressure. Measurement of PVR is made by subtracting pulmonary artery wedge pressure from the mean pulmonary arterial pressure and dividing by cardiac output in liters per minute.

(a) A further aspect of the present invention relates to macitentan for use in the treatment and/or prevention of CTEPH according to aspect (a), wherein the dosage of macitentan is 25 to 50 mg per day. Preferably, the dosage is 30 to 45 mg per day, more preferably 35 to 40 mg per day and most preferably 37.5 mg per day. It is to be understood that each of the lower limits disclosed above may be combined with each of the upper limits, i.e. the dosage could also be from 25 to 45 mg per day, or from 25 to 40 mg per day. Also disclosed are dosages from 30 to 50 mg, or 30 to 40 mg per day. A further preferred dosage range is 36 to 39 mg per day.

According to a more preferred aspect, these dosages are applied once a day.

(b) Another aspect of the present invention relates to macitentan for use in the treatment and/or prevention of CTEPH according to aspect (a), wherein the dosage of macitentan is 60 to 90 mg per day. Preferably, the dosage is 65 to 85 mg per day, more preferably the dosage is 70 to 80 mg per day and most preferably the dosage is 75 mg per day. It is to be understood that each of the lower limits disclosed above may be combined with each of the upper limits, i.e. the dosage could also be from 60 to 85 mg, from 60 to 80 mg, or from 60 to 75 mg per day. Also disclosed are dosages from 65 to 90 mg, or 65 to 75 mg per day. A further preferred dosage range is 72 to 78 mg per day.

According to a more preferred aspect, these dosages are applied once a day.

(c) A further aspect of the present invention relates to macitentan for use in the treatment and/or prevention of CTEPH according to aspect (a), wherein the dosage of macitentan is 100 to 200 mg per day. Preferably, the dosage is 125 to 175 mg per day, more preferably 140 to 160 mg per day and most preferably 150 mg per day. It is to be understood that each of the lower limits disclosed above may be combined with each of the upper limits, i.e. the dosage could also be from 100 to 175 mg per day, from 100 to 160 mg per day or from 100 to 150 mg per day. Also disclosed are dosages from 125 to 160 mg or 140 to 175 mg per day. A further preferred dosage range is 145 to 155 mg per day.

According to a more preferred aspect, these dosages are applied once a day.

(d) One aspect of the present invention relates to macitentan for use in the treatment and/or prevention of CTEPH according to any one of aspects (a) to (d), wherein the recited dosages are applied once a day.

(e) A further aspect of the present invention relates to macitentan for use in the treatment and/or prevention of CTEPH according to aspect (a), wherein the dosage of macitentan is 25 to 50 mg twice per day, preferably 30 to 45 mg twice per day, more preferably 35 to 40 mg twice per day and most preferably 37.5 mg twice per day. It is to be understood that each of the lower limits disclosed above may be combined with each of the upper limits, i.e. the dosage could also be from 25 to 45 mg twice per day, or from 25 to 40 mg twice per day. Also disclosed are dosages from 30 to 50 mg twice per day, or 30 to 40 mg twice per day. A further preferred dosage range is 36 to 39 mg twice per day.

(f) A further aspect of the present invention relates to macitentan for use in the treatment and/or prevention of CTEPH according to aspect (a), wherein the dosage of macitentan is 60 to 90 mg twice per day. Preferably, the dosage is 65 to 85 mg twice per day, more preferably 70 to 80 mg twice per day and most preferably 75 mg twice per day. It is to be understood that each of the lower limits disclosed above may be combined with each of the upper limits, i.e. the dosage could also be from 60 to 85 mg twice per day, from 60 to 80 mg twice per day, or from 60 to 75 mg twice per day. Also disclosed are dosages from 65 to 90 mg twice per day, or 65 to 75 mg twice per day. A further preferred dosage range is 72 to 78 mg twice per day.

(g) A further aspect of the present invention relates to macitentan for use in the treatment and/or prevention of CTEPH according to aspect (a), wherein the dosage of macitentan is escalated from 10 mg per day, followed by 25 to 50 mg per day, preferably 37.5 mg per day, and optionally followed by 60 to 90 mg per day, preferably 75 mg per day.

Therein "followed by 25 to 50 mg per day" means preferably, the dosage is 30 to 45 mg per day, more preferably 35 to 40 mg per day and most preferably 37.5 mg per day. It is to be understood that each of the lower limits disclosed may be combined with each of the upper limits, i.e. the dosage could also be from 25 to 45 mg per day, or from 25 to 40 mg per day. Also disclosed are dosages from 30 to 50 mg, or 30 to 40 mg per day. A further preferred dosage range is 36 to 39 mg per day. It is to be understood that any escalation to a higher dose may be followed by return to the lower dose in case the higher dose is not tolerated.

Moreover, the phrase "optionally followed by 60 to 90 mg per day" means preferably, the dosage is 65 to 85 mg per day, more preferably the dosage is 70 to 80 mg per day and most preferably the dosage is 75 mg per day. It is to be understood that each of the lower limits disclosed above may be combined with each of the upper limits, i.e. the dosage could also be from 60 to 85 mg, from 60 to 80 mg, or from 60 to 75 mg per day. Also disclosed are dosages from 65 to 90 mg, or 65 to 75 mg per day. A further preferred dosage range is 72 to 78 mg per day. It is to be understood that any escalation to a higher dose may be followed by return to the lower dose in case the higher dose is not tolerated.

According to a more preferred aspect, these dosages are applied once a day.

According to a further aspect, the first dosage is applied for 15-45 days, and the second dosage is also applied for 15 to 45 days in case a third dosage is envisaged. If no third dosage is envisaged, the second dosage may be applied as long as required by the patient.

In the MERIT-1 Study, the dosage of macitentan for use in the treatment of CTEPH was 10 mg per day. Patients obtaining this dosage of 10 mg per day may receive an immediate dose escalation to 37.5 mg per day, optionally followed by 75 mg per day.

A further aspect of the present invention relates to macitentan for use in the treatment and/or prevention of CTEPH according to aspect (a), wherein the dosage of macitentan is escalated from 10 mg per day, followed by 25 to 50 mg per day, preferably 37.5 mg per day, followed by 60 to 90 mg per day, preferably 75 mg per day, optionally followed by 100 to 200 mg per day, preferably 150 mg per day.

The phrase "optionally followed by 100 to 200 mg per day" means preferably, the dosage is 125 to 175 mg per day, more preferably 140 to 160 mg per day and most preferably 150 mg per day. It is to be understood that each of the lower limits disclosed above may be combined with each of the upper limits, i.e. the dosage could also be from 100 to 175 mg per day, from 100 to 160 mg per day or from 100 to 150 mg per day. Also disclosed are dosages from 125 to 160 mg or 140 to 175 mg per day. A further preferred dosage range is 145 to 155 mg per day. According to a more preferred aspect, these dosages are applied once a day.

(h) A further aspect of the present invention relates to macitentan for use in the treatment and/or prevention of CTEPH according to aspect (a), wherein the dosage of macitentan is escalated from 10 mg per day (preferably once a day), followed by 25 to 50 mg per day, preferably 37.5 mg per day (preferably once a day), followed by 37.5 mg twice a day.

It is to be understood that any escalation to a higher dose may be followed by return to the lower dose in case the higher dose is not tolerated.

A further aspect of the present invention relates to macitentan for use in the treatment and/or prevention of CTEPH according to aspect (a), wherein the dosage of macitentan is escalated from 10 mg per day, followed by 25 to 50 mg per day, preferably 37.5 mg per day, followed by 37.5 mg twice a day, optionally followed by 100 to 200 mg per day, preferably 150 mg per day.

The phrase "optionally followed by 100 to 200 mg per day" means preferably, the dosage is 125 to 175 mg per day, more preferably 140 to 160 mg per day and most preferably 150 mg per day, for instance as 75 mg twice per day. It is to be understood that each of the lower limits disclosed above may be combined with each of the upper limits, i.e. the dosage could also be from 100 to 175 mg per day, from 100 to 160 mg per day or from 100 to 150 mg per day. Also disclosed are dosages from 125 to 160 mg or 140 to 175 mg per day. A further preferred dosage range is 145 to 155 mg per day.

According to a further aspect, the first dosage is applied for 15-45 days, and the second or third dosage is also applied for 15 to 45 days in case a third or fourth dosage is envisaged. If no third dosage is envisaged, the second dosage may be applied as long as required by the patient.

In the MERIT-1 Study, the dosage of macitentan for use in the treatment of CTEPH was 10 mg per day. Patients obtaining this dosage may receive an immediate dose escalation to 37.5 mg per day, or 75 mg per day, optionally followed by 150 mg per day.

(i) A further aspect of the present invention relates to macitentan for use in the treatment and/or prevention of CTEPH according to aspect (h) or (i), wherein a lower dosage of macitentan is applied for 15 to 45 days in case it is followed by a higher dosage.

This aspect therefore describes a dosage regimen wherein an initial dosage of 10 mg macitentan per day is preferably applied for 15 to 45 days, then a dosage of 25 to 50 mg per day, preferably 37.5 mg per day (preferably once per day) is applied, and in case of a further dosage escalation, the application time of 25 to 50 mg per day is 15 to 45 days, followed by an application of 60 to 90 mg per day, preferably by 75 mg once per day or 37.5 mg twice per day. Analogously, the application time of 60 to 90 mg per day (preferably 75 mg per day) is applied for 15 to 45 days in case a higher dosage of 100 to 200 mg per day, preferably 150 mg per day or 75 mg twice per day would follow.

Therein, the term "15 to 45 days" means preferably 20 to 40 days, more preferably 21 to 35 days, and most preferably 28 to 30 days, i.e. about one month.

(k) A further aspect of the present invention relates to macitentan for use in the treatment and/or prevention of CTEPH according to aspect (a), wherein the dosage of macitentan is escalated from 10 mg once per day, followed by 60 to 90 mg per day, preferably by 75 mg once per day or 37.5 mg twice per day, optionally followed by 100 to 200 mg per day, preferably 150 mg per day.

The phrase "followed by 60 to 90 mg per day" means preferably, the dosage is 65 to 85 mg per day, more preferably the dosage is 70 to 80 mg per day and most preferably the dosage is 75 mg per day. It is to be understood that each of the lower limits disclosed above may be combined with each of the upper limits, i.e. the dosage could also be from 60 to 85 mg, from 60 to 80 mg, or from 60 to 75 mg per day. Also disclosed are dosages from 65 to 90 mg, or 65 to 75 mg per day. Further preferred ranges are 72 to 78 mg per day, or 36 to 39 mg twice per day.

The phrase "followed by 100 to 200 mg per day" means preferably, the dosage is 125 to 175 mg per day, more preferably 140 to 160 mg per day and most preferably 150 mg per day. It is to be understood that each of the lower limits disclosed above may be combined with each of the upper limits, i.e. the dosage could also be from 100 to 175 mg per day, from 100 to 160 mg per day or from 100 to 150 mg per day. Also disclosed are dosages from 125 to 160 mg or 140 to 175 mg per day. A further preferred dosage range is 145 to 155 mg per day. It is to be understood that any escalation to a higher dose may be followed by return to the lower dose in case the higher dose is not tolerated.

In a further aspect of (k), a lower dosage of macitentan is applied for 15 to 45 days in case it is followed by a higher dosage.

Therein, the term "15 to 45 days" means preferably 20 to 40 days, more preferably 21 to 35 days, and most preferably 28 to 30 days, i.e. about one month.

(l) A further aspect of the present invention relates to macitentan for use in the treatment and/or prevention of CTEPH according to aspect (a) or (b), wherein the dosage of macitentan is 25 to 50 mg per day, preferably 37.5 mg per day; provided that the patient is already treated with an endothelin receptor antagonist preferably selected from bosentan and ambrisentan.

Moreover, the phrase "25 to 50 mg per day" means preferably, the dosage is 30 to 45 mg per day, more preferably 35 to 40 mg per day and most preferably 37.5 mg per day. It is to be understood that each of the lower limits disclosed may be combined with each of the upper limits, i.e. the dosage could also be from 25 to 45 mg per day, or from 25 to 40 mg per day. Also disclosed are dosages from 30 to 50 mg, or 30 to 40 mg per day. A further preferred dosage range is 36 to 39 mg per day.

According to a more preferred aspect, these dosages are applied once a day.

It is to be understood, that optionally, the dosage of macitentan can be further raised to 60 to 90 mg per day, optionally followed by 100 to 200 mg per day. The dosage is thereby the same in respect of amount and escalation as disclosed in any one of aspects (h) to (k).

(m) A further aspect of the present invention relates to macitentan for use in the treatment and/or prevention of CTEPH according to aspect (a) or (c), wherein the dosage of macitentan is 60 to 90 mg per day, preferably 75 mg per day; provided that the patient is already treated with an endothelin receptor antagonist preferably selected from bosentan and ambrisentan.

The phrase "60 to 90 mg per day" means preferably, the dosage is 65 to 85 mg per day, more preferably the dosage is 70 to 80 mg per day and most preferably the dosage is 75 mg per day. It is to be understood that each of the lower limits disclosed above may be combined with each of the upper limits, i.e. the dosage could also be from 60 to 85 mg, from 60 to 80 mg, or from 60 to 75 mg per day. Also disclosed are dosages from 65 to 90 mg, or 65 to 75 mg per day. Further preferred ranges are 72 to 78 mg per day, or 36 to 39 mg twice per day.

It is to be understood, that optionally, the dosage of macitentan can be further raised to 100 to 200 mg per day. The dosage is thereby the same in respect of amount and escalation as disclosed in any one of aspects (h) to (k).

According to a more preferred aspect, these dosages are applied once a day.

(n) A further aspect of the present invention relates to macitentan for use in the treatment and/or prevention of CTEPH according to any one of aspects (a), (l) and (m), wherein the dosage of macitentan is 25 to 50 mg per day, preferably 37.5 mg per day, preferably for 15 to 45 days;

followed by 60 to 90 mg per day, preferably 75 mg per day; provided that the patient is already treated with an endothelin receptor antagonist preferably selected from bosentan and ambrisentan. It is to be understood that any escalation to a higher dose may be followed by return to the lower dose in case the higher dose is not tolerated.

Therein, the term "15 to 45 days" means preferably 20 to 40 days, more preferably 21 to 35 days, and most preferably 28 to 30 days, i.e. about one month.

Moreover, the phrase "25 to 50 mg per day" means preferably, the dosage is 30 to 45 mg per day, more preferably 35 to 40 mg per day and most preferably 37.5 mg per day. It is to be understood that each of the lower limits disclosed may be combined with each of the upper limits, i.e. the dosage could also be from 25 to 45 mg per day, or from 25 to 40 mg per day. Also disclosed are dosages from 30 to 50 mg, or 30 to 40 mg per day. Further preferred ranges are 36 to 39 mg per day.

Moreover, the phrase "followed by 60 to 90 mg per day" means preferably, the dosage is 65 to 85 mg per day, more preferably the dosage is 70 to 80 mg per day and most preferably the dosage is 75 mg per day. It is to be understood that each of the lower limits disclosed above may be combined with each of the upper limits, i.e. the dosage could also be from 60 to 85 mg, from 60 to 80 mg, or from 60 to 75 mg per day. Also disclosed are dosages from 65 to 90 mg, or 65 to 75 mg per day. Further preferred ranges are 72 to 78 mg per day, or 36 to 39 mg twice per day.

It is to be understood, that optionally, the dosage of macitentan can be further raised from 100 to 200 mg per day. The dosage is thereby escalated as in aspect (h) to (k).

According to a more preferred aspect, these dosages are applied once a day.

(o) A further aspect of the present invention relates to macitentan for use in the treatment and/or prevention of CTEPH according to any one of aspects (a) to (n), preferably (a) to (k), wherein macitentan is combined with a PDE5 inhibitor and/or a prostacyclin analogue, and/or a prostacyclin receptor agonist and/or a soluble guanylate cyclase stimulator.

PH is associated with upregulation of vascular PDE5, which rapidly degrades cGMP via which nitric oxide, a potent vasodilator, exerts its vasodilator effects. Nitric oxide is also reduced in PH. PDE5 inhibitors enhance nitric oxide-mediated vasodilation by decreasing the degradation of cGMP (i.e., by preserving cGMP). They also may have additional beneficial effects on platelet activation and pulmonary vascular remodeling. Sildenafil, a selective PDE5 inhibitor, significantly decreases PVR within 3 months of starting therapy in patients deemed inoperable or with residual PH after pulmonary endarterectomy (PEA) surgery. This initial improvement translates into significantly improved hemodynamics (including cardiac index), B-type natriuretic peptide (BNP) level, 6-minute walk distance, and symptom scores with 12 months of therapy, possibly suggesting that sildenafil has disease-modifying effects on the pulmonary vasculature [Suntharalingam et al., Long-term use of sildenafil in inoperable chronic thromboembolic pulmonary hypertension. *CHEST* (2008), 134, 229-236]. However, despite this limited study, sildenafil is not approved in CTEPH.

Prostanoids have several important effects on the vasculature; they are potent vasodilators that also inhibit vascular smooth muscle proliferation and platelet aggregation. Continuous intravenous (IV) administration of epoprostenol via infusion pump to patients with PVR greater than 1200 dynes·s·cm$^{-5}$ before PEA surgery may significantly increase preoperative cardiac output and reduces PVR [Jensen et al., Pulmonary hypertensive medical therapy in chronic thromboembolic pulmonary hypertension before pulmonary thromboendarterectomy. *Circulation* (2009), 120, 1248-1254; Nagaya et al., Prostacyclin therapy before pulmonary thromboendarterectomy in patients with chronic thromboembolic pulmonary hypertension. *CHEST* (2003), 123, 338-343]. An inhaled prostanoid, iloprost, also has been studied with variable results in CTEPH patients [Krug et al., Acute improved hemodynamics following inhaled iloprost in chronic thromboembolic pulmonary hypertension. *Respiration* (2008), 76, 154-159; Kramm et al., Inhaled iloprost in patients with chronic thromboembolic pulmonary hypertension: effects before and after pulmonary thromboendarterectomy. *Ann. Thorac. Surg.* (2003), 76, 711-718]. However, these prostanoids are not approved in CTEPH.

No Drug-Drug Interaction has been observed for macitentan and its active metabolite, ACT-132577 so far.

For example, macitentan 10 mg per day o.d. has not shown any effect on the pharmacokinetics of 1 mg rosuvastatin, which suggests that BCRP transporters have not been inhibited. BCRP is an efflux pump located in the gut, liver canalicular membrane, and kidney, and is exposed to intracellular drug concentrations in the liver and the kidney.

Macitentan and ACT-132577 activated human PXR with $EC_{50}$ values of 1.1 to 1.2 µM and 7.2 to 8.7 µM, respectively. In human hepatocytes, both compounds elicited concentration-dependent increases in CYP3A4 mRNA and enzyme activity.

Predicted peak plasma concentrations of macitentan and ACT-132577 in PAH patients at 75 mg per day dose are expected to be around 5 µM and 14 µM, respectively, based on the PK Sub-study and assuming dose linearity. Taking into account the high degree of protein binding, free plasma concentrations are expected to be in the range of 0.02 µM to 0.07 µM for macitentan and ACT-132577, respectively. It is not likely that these unbound concentrations of macitentan and ACT-132577 result in any inhibition of BCRP in the liver or kidney or induction of CYP3A4 enzyme in the liver.

Therefore, the dosage of macitentan may be 60 to 90 mg per day in aspect (o). Preferably, the dosage is 65 to 85 mg per day, more preferably the dosage is 70 to 80 mg per day and most preferably the dosage is 75 mg per day. It is to be understood that each of the lower limits disclosed above may be combined with each of the upper limits, i.e. the dosage could also be from 60 to 85 mg, from 60 to 80 mg, or from 60 to 75 mg per day. Also disclosed are dosages from 65 to 90 mg, or 65 to 75 mg per day. A further preferred dosage range is 72 to 78 mg per day.

Further, the dosage of macitentan may be escalated from 10 mg per day, followed by 25 to 50 mg per day, preferably 37.5 mg per day, followed by 60 to 90 mg per day, preferably 75 mg per day, optionally followed by 100 to 200 mg per day, preferably 150 mg per day.

(p) A further aspect of the present invention relates to macitentan for use in the treatment and/or prevention of CTEPH according to aspect (o), wherein the PDE5 inhibitor is selected from sildenafil, tadalafil, vardenafil, and udenafil; the prostacyclin analogue is selected from epoprostenol, treprostinil, iloprost, and beraprost; the prostacyclin receptor agonist is selected from selexipag and ralinepag; and the soluble guanylate cyclase stimulator is selected from riociguat, olinciguat, praliciguat and vericiguat.

Therein, macitentan has a dosage or dosage regimen according to any one of aspects (a) to (n) and (o).

(q) A further aspect of the present invention relates to macitentan for use in the treatment and/or prevention of CTEPH according to aspect (o) or (p), wherein macitentan is combined with tadalafil and/or selexipag and/or riociguat, preferably with riociguat.

Therein, macitentan has a dosage or dosage regimen according to any one of aspects (a) to (n) and (o).

(r) A further aspect of the present invention relates to macitentan for use in the treatment and/or prevention of CTEPH according to aspect (q), wherein tadalafil, if applicable, has a dosage of 20 to 40 mg per day, selexipag, if applicable, has a dosage of 0.2 to 1.6 mg twice per day, and riociguat, if applicable, has a dosage of 0.5 mg three times per day to 2.5 mg three times per day.

Preferably, macitentan for use in the treatment and/or prevention of CTEPH according to aspect (o) or (p), is combined with riociguat at a dosage of 0.5 mg three times per day to 2.5 mg three times per day.

It is to be understood that in the instances above the dosage of riociguat of 0.5 mg three times per day is used in case a patient does not tolerate a dosage of 1 mg three times per day. Preferred dosages of riociguat are 1 mg three times per day to 2.5 mg three times per day, including 1.5 mg three times per day and 2 mg three times per day. More preferred is 2.5 mg three times per day.

Therein, macitentan has a dosage or dosage regimen according to any one of aspects (a) to (n) and (o).

(s) A further aspect of the present invention relates to macitentan for use in specific patient populations in need of a treatment with macitentan according to any dosage, dosage regimen or combination described in any one of aspects (a) to (r).

(s)(i) A further aspect of the present invention relates to macitentan for use in the treatment and/or prevention of CTEPH according to any one of aspects (a) to (r), wherein macitentan is for use in patients before PEA surgery. In this aspect, the patients are selected from patients which are candidates for PEA surgery, before they undergo PEA surgery.

Pulmonary endarterectomy (PEA) should be offered to all eligible patients with CTEPH. The international registry of incident cases of CTEPH reported 3-year survival of 90% in those operated and 70% in those not having surgery [Delcroix et al., Long-term outcome of patients with chronic thromboembolic pulmonary hypertension: results from an international prospective registry. *Circulation* (2016), 133, 859-871]. While select patients may be technically operable, they may not benefit from PEA due to significant comorbidities [Kim et al., Chronic thromboembolic pulmonary hypertension. *Eur. Respir. J.* (2018), in press (https://doi.org/10.1183/13993003.01915-2018)] or other reasons.

According to the surgical classification of chronic thromboembolic pulmonary hypertension of the University of California, San Diego (UCSD), there are 5 surgical levels [Madani et al., Pulmonary endarterectomy. Patient selection, technical challenges, and outcomes. *Ann. Am. Thorac. Soc.* (2016), 13(Suppl. 3), S240-S247]:

In surgical level 0, there is no evidence of thromboembolic disease in either lung.

In surgical level I, chronic thromboembolism (CTE) is starting in the main pulmonary arteries. According to a sub-level IC, there is a complete occlusion of one main pulmonary artery with CTE.

In surgical level II, chronic thromboembolism (CTE) is starting at the level of lobar arteries or in the main descending pulmonary arteries.

In surgical level III, chronic thromboembolism (CTE) is starting at the level of the segmental arteries.

In surgical level IV, chronic thromboembolism (CTE) is starting at the level of the subsegmental arteries.

In one aspect of the present invention, PEA surgery encompasses preferably surgical levels I to IV according to the classification of UCSD.

(s)(ii) A further aspect of the present invention relates to macitentan for use in the treatment and/or prevention of CTEPH according to any one of aspects (a) to (r), wherein the patient to be treated is inoperable with PEA surgery. In this aspect, the patients with CTEPH are not candidates for PEA surgery, i.e. they are inoperable patients.

While PEA remains the treatment of choice for most patients with CTEPH, around 40% of the patients in the international CTEPH registry are considered inoperable due to concern for inaccessible vascular obstruction, PAP out of proportion to morphological lesions and significant prohibitive comorbidities [Pepke-Zaba et al., Chronic thromboembolic pulmonary hypertension (CTEPH): results from an international prospective registry. *Circulation* (2011), 124, 1973-1981].

Such a patient population with inoperable CTEPH is preferred and treated with macitentan according to any one of aspects (a) to (r).

(s)(iii) A further aspect of the present invention relates to macitentan for use in the treatment and/or prevention of CTEPH according to any one of aspects (a) to (r), wherein the patient to be treated suffers from persistent or recurrent PH after PEA surgery. In this aspect, the patients have undergone PEA surgery and have persistent or recurrent pulmonary hypertension (PH). Therein, the PH after surgery is defined as mPAP>20 mm Hg and PVR≥240 dynes sec $cm^{-5}$. Therein, each Wood unit is 80 dynes·sec·$cm^{-5}$.

(s)(iv) A further aspect of the present invention relates to macitentan for use in the treatment and/or prevention of CTEPH according to any one of aspects (a) to (r), wherein the patient to be treated is treated with balloon pulmonary angioplasty (BPA) and PEA surgery. In this aspect, the patients with CTEPH are candidates for BPA procedure, independently at which time point they undergo PEA surgery.

BPA has been reported to improve haemodynamics, symptoms, exercise capacity and right ventricular function [Ogo, Balloon pulmonary angioplasty for inoperable chronic thromboembolic pulmonary hypertension. *Curr. Opin. Pulm. Med.* (2015), 21, 425-431]. According to a further aspect of the present invention, macitentan is applied according to any one of aspects (a) to (r) in patients with CTEPH who have been treated with BPA, before PEA surgery.

(s)(v) A further aspect of the present invention relates to macitentan for use in the treatment and/or prevention of CTEPH according to any one of aspects (a) to (r), wherein the patient to be treated is excluded from BPA. In this aspect, the patients with CTEPH are not candidates for BPA procedure, i.e. patients are excluded from BPA.

(s)(vi) A further aspect of the present invention relates to macitentan for use in the treatment and/or prevention of CTEPH according to any one of aspects (a) to (r), wherein the patient to be treated suffers from persistent or recurrent PH after BPA. In this aspect, the patients with CTEPH have undergone BPA procedure and still suffer from persistent or recurrent PH. The PH after surgery is defined as mPAP>20 mm Hg and PVR≥240 dyn s $cm^{-5}$. Therein, each Wood unit is 80 dynes·sec·$cm^{-5}$.

(t) A further aspect of the present invention relates to a pharmaceutical composition for use in the treatment of CTEPH comprising macitentan and at least a pharmaceutically acceptable excipient, containing macitentan in an amount of 20 mg to 300 mg, for example, 20 mg to 250 mg, preferably 37.5 mg, 75 mg or 150 mg, more preferably 37.5 mg or 75 mg, most preferably 75 mg.

It is to be understood that macitentan may have a dosage according to any one of the daily dosages of aspects (a) to (s)(vi).

(u) A further aspect of the present invention relates to the pharmaceutical composition according to aspect (t), which comprises
 i) macitentan in a total amount of 10 to 50% in weight based on the total weight of the pharmaceutical composition,
 ii) a filler, consisting of lactose monohydrate with microcrystalline cellulose, in a total amount of 10 to 85% in weight based on the total weight of the pharmaceutical composition,
 iii) a disintegrant, consisting of sodium starch glycolate or a combination of sodium starch glycolate and polyvinylpyrrolidone, in a total amount of 1 to 10% in weight based on the total weight of the pharmaceutical composition,
 iv) a surfactant, consisting of a polysorbate, in a total amount of 0.1 to 1% in weight based on the total weight of the pharmaceutical composition, and
 v) a lubricant, consisting of magnesium stearate, in a total amount of 0.05 to 5% in weight based on the total weight of the pharmaceutical composition.

(v) A further aspect of the present invention relates to the pharmaceutical composition according to aspect (t) or (u), which is in the form of a capsule or a tablet (in particular in the form of a tablet, notably a tablet containing 37.5 mg or 75 mg preferably of 75 mg of macitentan).

(w) A further aspect of the present invention relates to macitentan for use in the treatment and/or prevention of CTEPH according to any one of aspects (a) to (s), wherein the treatment and/or prevention means the reduction of morbidity and/or mortality risk of CTEPH. That is, this aspect of the present invention relates to macitentan for use in reducing morbidity and/or mortality risk of CTEPH, in which macitentan is used in a manner according to any one of aspects (a) to (s).

The reduction of morbidity and/or mortality risk of CTEPH may be evaluated as the reduction of the composite morbidity/mortality risk, for example, by time to first clinical worsening up to 7 days after EOT (End of Treatment), defined as time from baseline to the first of the following events (the primary endpoint):
 Death (all-cause mortality);
 Pulmonary hypertension related hospitalization (including for worsening of CTEPH, atrial septostomy, lung transplantation with or without heart transplantation, or initiation of parenteral prostacyclins);
 Worsening of CTEPH resulting in initiation of parenteral prostanoid therapy;
 Pulmonary hypertension related disease progression, defined as:
  For functional class II and III patients at baseline (both criteria have to be satisfied):
   More than 15% decrease in 6MWD from baseline, confirmed by two 6MWD tests performed on separate days within 2 weeks of each other;
   Initiation of additional CTEPH therapy or Worsening of WHO Functional Class;
  For functional class IV patients at baseline (both criteria have to be satisfied):
   More than 15% decrease in 6MWD from baseline, confirmed by two 6MWD tests performed on separate days within 2 weeks of each other;
   Initiation of additional CTEPH therapy.

Alternatively, the reduction of morbidity and/or mortality risk of CTEPH may be evaluated separately. For example, 6MWD may be employed as the primary end point for evaluating the reduction of morbidity risk of CTEPH.

The above evaluation may be made for example by the following schedule:
 i) Run-in period (for example 4 weeks) with the dosage of macitentan of 10 mg per day;
 ii) Titration period (for example 4 weeks) with the dosage of macitentan of 37.5 mg per day;
 iii) Maintenance period with the dosage of macitentan of 75 mg per day.

The above evaluation may be made for example by a double blind test with the control group receiving the dosage of macitentan of 10 mg per day in the titration and maintenance period.

For reducing the morbidity and/or mortality risk of CTEPH, the dosage of macitentan may be 60 to 90 mg per day. Preferably, the dosage is 65 to 85 mg per day, more preferably the dosage is 70 to 80 mg per day and most preferably the dosage is 75 mg per day. It is to be understood that each of the lower limits disclosed above may be combined with each of the upper limits, i.e. the dosage could also be from 60 to 85 mg, from 60 to 80 mg, or from 60 to 75 mg per day. Also disclosed are dosages from 65 to 90 mg, or 65 to 75 mg per day. A further preferred dosage range is 72 to 78 mg per day.

Further, the dosage of macitentan may be escalated from 10 mg per day, followed by 25 to 50 mg per day, preferably 37.5 mg per day, followed by 60 to 90 mg per day, preferably 75 mg per day, optionally followed by 100 to 200 mg per day, preferably 150 mg per day.

It is to be understood that all disclosed aspects are to be regarded as disclosed also in the form of macitentan for the manufacture of a medicament for the uses according to any one of aspects (a) to (s)(vi) and (w).

(a') One aspect of the present invention relates to macitentan for the manufacture of a medicament for use in the treatment and/or prevention of chronic thromboembolic pulmonary hypertension (CTEPH) in human, wherein the dosage of macitentan is from 20 mg per day to 300 mg per day, for example, 20 mg per day to 250 mg per day, preferably from 25 mg per day to 200 mg per day and more preferably from 25 mg per day to 150 mg per day. It is to be understood that the disclosure of aspect (a) applies analogously.

(b') Another aspect of the present invention relates to macitentan for the manufacture of a medicament for use in the treatment and/or prevention of CTEPH according to aspect (a'), wherein the dosage of macitentan is 25 to 50 mg per day, preferably 30 to 45 mg per day, more preferably 35 to 40 mg per day and most preferably 37.5 mg per day. It is to be understood that the disclosure of aspect (b) applies analogously.

(c') Another aspect of the present invention relates to macitentan for the manufacture of a medicament for use in the treatment and/or prevention of CTEPH according to aspect (a'), wherein the dosage of macitentan is 60 to 90 mg per day, preferably 65 to 85 mg per day, more preferably 70 to 80 mg per day and most preferably 75 mg per day. It is to be understood that the disclosure of aspect (c) applies analogously.

(d') Another aspect of the present invention relates to macitentan for the manufacture of a medicament for use in the treatment and/or prevention of CTEPH according to aspect (a'), wherein the dosage of macitentan is 100 to 200 mg per day, preferably 125 to 175 mg per day, more preferably 140 to 160 mg per day and most preferably 150 mg per day. It is to be understood that the disclosure of aspect (d) applies analogously.

(e') Another aspect of the present invention relates to macitentan for the manufacture of a medicament for use in the treatment and/or prevention of CTEPH according to any one of aspects (a') to (d'), wherein the dosages are given once per day. It is to be understood that the disclosure of aspect (e) applies analogously.

(f') Another aspect of the present invention relates to macitentan for the manufacture of a medicament for use in the treatment and/or prevention of CTEPH according to aspect (a'), wherein the dosage of macitentan is 25 to 50 mg twice per day, preferably 30 to 45 mg twice per day, more preferably 35 to 40 mg twice per day and most preferably 37.5 mg twice per day. It is to be understood that the disclosure of aspect (f) applies analogously.

(g') Another aspect of the present invention relates to macitentan for the manufacture of a medicament for use in the treatment and/or prevention of CTEPH according to aspect (a'), wherein the dosage of macitentan is 60 to 90 mg twice per day, preferably 65 to 85 mg twice per day, more preferably 70 to 80 mg twice per day and most preferably 75 mg twice per day. It is to be understood that the disclosure of aspect (g) applies analogously.

(h') Another aspect of the present invention relates to macitentan for the manufacture of a medicament for use in the treatment and/or prevention of CTEPH according to aspect (a'), wherein the dosage of macitentan is escalated from 10 mg per day, followed by 25 to 50 mg per day, preferably 37.5 mg per day, and optionally followed by 60 to 90 mg per day, preferably 75 mg per day. It is to be understood that the disclosure of aspect (h) applies analogously.

(i') Another aspect of the present invention relates to macitentan for the manufacture of a medicament for use in the treatment and/or prevention of CTEPH according to aspect (a'), wherein the dosage of macitentan is escalated from 10 mg per day, followed by 25 to 50 mg per day, preferably 37.5 mg per day, followed by 37.5 mg twice a day. It is to be understood that the disclosure of aspect (i) applies analogously.

(j') Another aspect of the present invention relates to macitentan for the manufacture of a medicament for use in the treatment and/or prevention of CTEPH according to aspect (h') or (i'), wherein the lower dosage of macitentan is applied for 15 to 45 days in case it is followed by a higher dose. It is to be understood that the disclosure of aspect (j) applies analogously.

(k') Another aspect of the present invention relates to macitentan for the manufacture of a medicament for use in the treatment and/or prevention of CTEPH according to aspect (a') wherein the dosage of macitentan is escalated from 10 mg once per day, followed by 60 to 90 mg per day, preferably by 75 mg once per day or 37.5 mg twice per day, optionally followed by 100 to 200 mg per day, preferably 150 mg per day.

In a further aspect of (k'), a lower dosage of macitentan is applied for 15 to 45 days in case it is followed by a higher dose. It is to be understood that the disclosure of aspect (k) applies analogously.

(l') Another aspect of the present invention relates to macitentan for the manufacture of a medicament for use in the treatment and/or prevention of CTEPH according to any one of aspects (a') or (b'), wherein the dosage of macitentan is 25 to 50 mg per day, preferably 37.5 mg per day, provided that the medicament is for patients already treated with an endothelin receptor antagonist preferably selected from bosentan and ambrisentan. It is to be understood that the disclosure of aspect (l) applies analogously.

(m') Another aspect of the present invention relates to macitentan for the manufacture of a medicament for use in the treatment and/or prevention of CTEPH according to any one of aspects (a') or (c'), wherein the dosage of macitentan is 60 to 90 mg per day, preferably 75 mg per day; provided that the medicament is for patients already treated with an endothelin receptor antagonist preferably selected from bosentan and ambrisentan. It is to be understood that the disclosure of aspect (m) applies analogously.

(n') Another aspect of the present invention relates to macitentan for the manufacture of a medicament for use in the treatment and/or prevention of CTEPH according to any one of aspects (a'), (l') or (m'), wherein the dosage of macitentan is 25 to 50 mg per day, preferably 37.5 mg per day, preferably for 15 to 45 days; followed by 60 to 90 mg per day, preferably 75 mg per day; provided that the medicament is for patients already treated with an endothelin receptor antagonist preferably selected from bosentan and ambrisentan. It is to be understood that the disclosure of aspect (n) applies analogously.

(o') Another aspect of the present invention relates to macitentan for the manufacture of a medicament for use in the treatment and/or prevention of CTEPH according to any one of aspects (a') to (n'), preferably any one of aspects (a') to (k'), wherein macitentan is for use in combination with a PDE5 inhibitor and/or a prostacyclin analogue, and/or a prostacyclin receptor agonist and/or a soluble guanylate cyclase stimulator. It is to be understood that the disclosure of aspect (o) applies analogously.

(p') Another aspect of the present invention relates to macitentan for the manufacture of a medicament for use in the treatment and/or prevention of CTEPH according to aspect (o'), wherein the PDE5 inhibitor is selected from sildenafil, tadalafil, vardenafil, and udenafil; the prostacyclin analogue is selected from epoprostenol, treprostinil, iloprost, and beraprost; the prostacyclin receptor agonist is selected from selexipag and ralinepag; and the soluble guanylate cyclase stimulator is selected from riociguat, olinciguat, praliciguat and vericiguat. It is to be understood that the disclosure of aspect (p) applies analogously.

(q') Another aspect of the present invention relates to macitentan for the manufacture of a medicament for use in the treatment and/or prevention of CTEPH according to aspect (o') or (p'), wherein macitentan is for use in combination with tadalafil and/or selexipag and/or riociguat, preferably with riociguat. It is to be understood that the disclosure of aspect (q) applies analogously.

(r') Another aspect of the present invention relates to macitentan for the manufacture of a medicament for use in the treatment and/or prevention of CTEPH according to aspect (q'), wherein tadalafil, if applicable, has a dosage of 20 to 40 mg per day, selexipag, if applicable, has a dosage of 0.2 to 1.6 mg twice per day, and riociguat, if applicable, has a dosage of 0.5 mg three times per day to 2.5 mg three times per day, preferably 2.5 mg three times per day. It is to be understood that the disclosure of aspect (r) applies analogously.

(s') A further aspect of the present invention relates to macitentan for the manufacture of a medicament for use in the treatment and/or prevention of specific patient populations with CTEPH.

(s')(i) A further aspect of the present invention relates to macitentan for the manufacture of a medicament for use in the treatment and/or prevention of CTEPH according to any one of aspects (a') to (r'), wherein the medicament is for patients before PEA surgery. It is to be understood that the disclosure of aspect (s)(i) applies analogously.

(s')(ii) A further aspect of the present invention relates to macitentan for the manufacture of a medicament for use in the treatment and/or prevention of CTEPH according to any one of aspects (a') to (r'), wherein the medicament is for patients inoperable with PEA surgery. It is to be understood that the disclosure of aspect (s)(ii) applies analogously.

(s')(iii) A further aspect of the present invention relates to macitentan for the manufacture of a medicament for use in the treatment and/or prevention of CTEPH according to any one of aspects (a') to (r'), wherein the medicament is for patients suffering from persistent or recurrent PH after PEA surgery. It is to be understood that the disclosure of aspect (s)(iii) applies analogously.

(s')(iv) A further aspect of the present invention relates to macitentan for the manufacture of a medicament for use in the treatment and/or prevention of CTEPH according to any one of aspects (a') to (r'), wherein the medicament is for patients treated with BPA and PEA surgery. It is to be understood that the disclosure of aspect (s)(iv) applies analogously.

(s')(v) A further aspect of the present invention relates to macitentan for the manufacture of a medicament for use in the treatment and/or prevention of CTEPH according to any one of aspects (a') to (r'), wherein the medicament is for patients excluded from BPA. It is to be understood that the disclosure of aspect (s)(v) applies analogously.

(s')(vi) A further aspect of the present invention relates to macitentan for the manufacture of a medicament for use in the treatment and/or prevention of CTEPH according to any one of aspects (a') to (r'), wherein the medicament is for patients suffering from persistent or recurrent PH after BPA. It is to be understood that the disclosure of aspect (s)(vi) applies analogously.

(w') Another aspect of the present invention relates to macitentan for the manufacture of a medicament for use in the treatment and/or prevention of CTEPH according to any one of aspects (a') to (s'), wherein the treatment and/or prevention means the reduction of morbidity and/or mortality risk of CTEPH. That is, this aspect of the present invention relates to macitentan for the manufacture of a medicament in reducing morbidity and/or mortality risk of CTEPH, in which macitentan is used in a manner according to any one of aspects (a') to (s'). It is to be understood that the disclosure of aspect (w) applies analogously.

Moreover, it is to be understood that all disclosed aspects (a) to (s)(vi) and (w) are to be regarded as disclosed also in the form of a method of treatment.

(a") One aspect of the present invention relates to a method of treatment and/or prevention of chronic thromboembolic pulmonary hypertension (CTEPH) in human, said method comprising administering macitentan to a patient in need thereof at a dosage of 20 mg per day to 300 mg per day, for example, 20 mg per day to 250 mg per day, preferably from 25 mg day to 200 mg per day and more preferably from 25 mg per day to 150 mg per day. It is to be understood that the disclosure of aspect (a) applies analogously.

(b") Another aspect of the present invention relates to a method of treatment and/or prevention of chronic thromboembolic pulmonary hypertension (CTEPH) in human according to aspect (a"), said method comprising administering macitentan to a patient in need thereof at a dosage of 25 to 50 mg per day, preferably 30 to 45 mg per day, more preferably 35 to 40 mg per day and most preferably 37.5 mg per day. It is to be understood that the disclosure of aspect (b) applies analogously.

(c") Another aspect of the present invention relates to a method of treatment and/or prevention of chronic thromboembolic pulmonary hypertension (CTEPH) in human according to aspect (a"), said method comprising administering macitentan to a patient in need thereof at a dosage of 60 to 90 mg per day, preferably 65 to 85 mg per day, more preferably 70 to 80 mg per day and most preferably 75 mg per day. It is to be understood that the disclosure of aspect (c) applies analogously.

(d") Another aspect of the present invention relates to a method of treatment and/or prevention of chronic thromboembolic pulmonary hypertension (CTEPH) in human according to aspect (a"), said method comprising administering macitentan to a patient in need thereof at a dosage of 100 to 200 mg per day, preferably 125 to 175 mg per day, more preferably 140 to 160 mg per day and most preferably 150 mg per day. It is to be understood that the disclosure of aspect (d) applies analogously.

(e") Another aspect of the present invention relates to macitentan for the manufacture of a medicament for use in the treatment and/or prevention of CTEPH according to any one of aspects (a") to (d"), wherein the dosages are given once per day. It is to be understood that the disclosure of aspect (e) applies analogously.

(f") Another aspect of the present invention relates to a method of treatment and/or prevention of chronic thromboembolic pulmonary hypertension (CTEPH) in human according to aspect (a"), said method comprising administering macitentan to a patient in need thereof at a dosage of 25 to 50 mg twice per day, preferably 30 to 45 mg twice per day, more preferably 35 to 40 mg twice per day and most preferably 37.5 mg twice per day. It is to be understood that the disclosure of aspect (f) applies analogously.

(g") Another aspect of the present invention relates to a method of treatment and/or prevention of chronic thromboembolic pulmonary hypertension (CTEPH) in human according to aspect (a"), said method comprising administering macitentan to a patient in need thereof at a dosage of 60 to 90 mg twice per day, preferably 65 to 85 mg twice per day, more preferably 70 to 80 mg twice per day and most preferably 75 mg twice per day. It is to be understood that the disclosure of aspect (g) applies analogously.

(h") Another aspect of the present invention relates to a method of treatment and/or prevention of chronic thromboembolic pulmonary hypertension (CTEPH) in human according to aspect (a"), said method comprising administering macitentan to a patient in need thereof at a dosage of 10 mg per day, followed by 25 to 50 mg per day, preferably 37.5 mg per day, and optionally followed by 60 to 90 mg per day, preferably 75 mg per day. It is to be understood that the disclosure of aspect (h) applies analogously.

(i") Another aspect of the present invention relates to a method of treatment and/or prevention of chronic thromboembolic pulmonary hypertension (CTEPH) in human according to aspect (a"), said method comprising administering macitentan to a patient in need thereof at a dosage of 10 mg per day, followed by 25 to 50 mg per day, preferably 37.5 mg per day, followed by 37.5 mg twice a day. It is to be understood that the disclosure of aspect (i) applies analogously.

(j") Another aspect of the present invention relates to a method of treatment and/or prevention of chronic thromboembolic pulmonary hypertension (CTEPH) in human according to aspect (h") or (i"), wherein the lower dosage of macitentan is applied for 15 to 45 days in case it is followed by a higher dose. It is to be understood that the disclosure of aspect (j) applies analogously.

(k") Another aspect of the present invention relates to a method of treatment and/or prevention of chronic thromboembolic pulmonary hypertension (CTEPH) in human according to aspect (a"), said method comprising administering macitentan to a patient in need thereof at a dosage of 10 mg once per day, followed by 60 to 90 mg per day, preferably by 75 mg once per day or 37.5 mg twice per day, optionally followed by 100 to 200 mg per day, preferably 150 mg per day.

In a further aspect of (k"), the lower dosage of macitentan is applied for 15 to 45 days in case it is followed by a higher dose.

It is to be understood that the disclosure of aspect (k) applies analogously.

(l") Another aspect of the present invention relates to a method of treatment and/or prevention of chronic thromboembolic pulmonary hypertension (CTEPH) in human according to aspect (a") or (b"), said method comprising administering macitentan to a patient in need thereof at a dosage of 25 to 50 mg per day, preferably 37.5 mg per day, provided that the patient is already treated with an endothelin receptor antagonist preferably selected from bosentan and ambrisentan. It is to be understood that the disclosure of aspect (l) applies analogously.

(m") Another aspect of the present invention relates to a method of treatment and/or prevention of chronic thromboembolic pulmonary hypertension (CTEPH) in human according to aspect (a") or (c"), said method comprising administering macitentan to a patient in need thereof at a dosage of 60 to 90 mg per day, preferably 75 mg per day; provided that the patient is already treated with an endothelin receptor antagonist preferably selected from bosentan and ambrisentan. It is to be understood that the disclosure of aspect (m) applies analogously.

(n") Another aspect of the present invention relates to a method of treatment and/or prevention of chronic thromboembolic pulmonary hypertension (CTEPH) in human according to any one of aspects (a"), (l") and (m"), said method comprising administering macitentan to a patient in need thereof at a dosage of 25 to 50 mg per day, preferably 37.5 mg per day, preferably for 15 to 45 days; followed by 60 to 90 mg per day, preferably 75 mg per day; provided that the patient is already treated with an endothelin receptor antagonist preferably selected from bosentan and ambrisentan. It is to be understood that the disclosure of aspect (n) applies analogously.

(o") Another aspect of the present invention relates to a method of treatment and/or prevention of chronic thromboembolic pulmonary hypertension (CTEPH) in human according to any one of aspects (a") to (n"), preferably any one of aspects (a") to (k"), wherein macitentan is combined with a PDE5 inhibitor and/or a prostacyclin analogue, and/or a prostacyclin receptor agonist and/or a soluble guanylate cyclase stimulator. It is to be understood that the disclosure of aspect (o) applies analogously.

(p") Another aspect of the present invention relates to a method of treatment and/or prevention of chronic thromboembolic pulmonary hypertension (CTEPH) in human according to aspect (o"), wherein the PDE5 inhibitor is selected from sildenafil, tadalafil, vardenafil, and udenafil; the prostacyclin analogue is selected from epoprostenol, treprostinil, iloprost, and beraprost; the prostacyclin receptor agonist is selected from selexipag and ralinepag; and the soluble guanylate cyclase stimulator is selected from riociguat, olinciguat, praliciguat and vericiguat. It is to be understood that the disclosure of aspect (p) applies analogously.

(q") Another aspect of the present invention relates to a method of treatment and/or prevention of chronic thromboembolic pulmonary hypertension (CTEPH) in human according to aspect (o") or (p"), wherein macitentan is combined with tadalafil and/or selexipag and/or riociguat, preferably with riociguat. It is to be understood that the disclosure of aspect (q) applies analogously.

(r") Another aspect of the present invention relates to a method of treatment and/or prevention of chronic thromboembolic pulmonary hypertension (CTEPH) in human according to aspect (q"), wherein tadalafil, if applicable, has a dosage of 20 to 40 mg per day, selexipag, if applicable, has a dosage of 0.2 to 1.6 mg twice per day, and riociguat, if applicable, has a dosage of 0.5 mg three times per day to 2.5 mg three times per day. It is to be understood that the disclosure of aspect (r) applies analogously.

(s") Another aspect of the present invention relates to a method of treatment and/or prevention of chronic thromboembolic pulmonary hypertension (CTEPH) in specific patient populations with CTEPH.

(s")(i) Another aspect of the present invention relates to a method of treatment and/or prevention of chronic thromboembolic pulmonary hypertension (CTEPH) in human according to any one of aspects (a") to (r"), wherein macitentan is applied before PEA surgery. It is to be understood that the disclosure of aspect (s)(i) applies analogously.

(s")(ii) Another aspect of the present invention relates to a method of treatment and/or prevention of chronic thromboembolic pulmonary hypertension (CTEPH) in human according to any one of aspects (a") to (r"), wherein the patient is inoperable with PEA surgery. It is to be understood that the disclosure of aspect (s)(ii) applies analogously.

(s")(iii) Another aspect of the present invention relates to a method of treatment and/or prevention of chronic thromboembolic pulmonary hypertension (CTEPH) in human according to any one of aspects (a") to (r"), wherein the patient suffers from persistent or recurrent PH after PEA surgery. It is to be understood that the disclosure of aspect (s)(iii) applies analogously.

(s")(iv) Another aspect of the present invention relates to a method of treatment and/or prevention of chronic thromboembolic pulmonary hypertension (CTEPH) in human according to any one of aspects (a") to (r"), wherein the patient is treated with BPA and PEA surgery. It is to be understood that the disclosure of aspect (s)(iv) applies analogously.

(s")(v) Another aspect of the present invention relates to a method of treatment and/or prevention of chronic thromboembolic pulmonary hypertension (CTEPH) in human according to any one of aspects (a") to (r"), wherein the patient is excluded from BPA. It is to be understood that the disclosure of aspect (s)(v) applies analogously.

(s")(vi) Another aspect of the present invention relates to a method of treatment and/or prevention of chronic thromboembolic pulmonary hypertension (CTEPH) in human according to any one of aspects (a") to (r"), wherein the patient suffers from persistent or recurrent PH after BPA. It is to be understood that the disclosure of aspect (s)(vi) applies analogously.

(w") Another aspect of the present invention relates to a method of treatment and/or prevention of CTEPH according to any one of aspects (a") to (s"), wherein the treatment and/or prevention means the reduction of morbidity and/or mortality risk of CTEPH. That is, this aspect of the present invention relates to a method of reducing morbidity and/or mortality risk of CTEPH, in which macitentan is used in a manner according to any one of aspects (a") to (s"). It is to be understood that the disclosure of aspect (w) applies analogously.

According to a further aspect of the present invention, in each of the above-mentioned aspects, that is, in each of aspects (a) to (v) and (w), (a') to (s')(vi) and (w') as well as (a") to (s")(vi) and (w"), macitentan can be replaced by its active metabolite, known under the code name ACT-132577 and the International Non-proprietary Name aprocitentan, which has the chemical formula

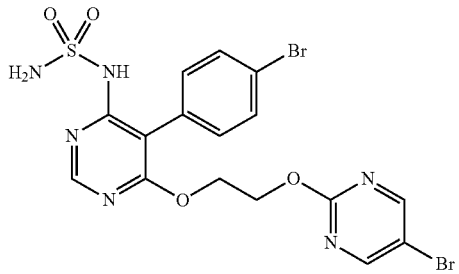 [SMILES: NS(=O)(=O)Nc1ncnc(OCCOc2ncc(Br)cn2)c1-c1ccc(Br)cc1]

whereby any weight amount of macitentan will be replaced a 5-fold weight amount of aprocitentan.

For example, taking aspect (c) of the invention described above, a further aspect of the invention relates to aprocitentan for use in the treatment and/or prevention of CTEPH according to aspect (a) wherein the weight amounts of macitentan will be replaced by 5-fold weight amounts of aprocitentan, wherein the dosage of aprocitentan is 300 to 450 mg per day. Preferably, the dosage of aprocitentan is 325 to 425 mg per day, more preferably the dosage of aprocitentan is 350 to 400 mg per day and most preferably the dosage of aprocitentan is 375 mg per day. It is to be understood that each of the lower limits disclosed above may be combined with each of the upper limits, i.e. the dosage of aprocitentan could also be from 300 to 425 mg, from 300 to 400 mg, or from 300 to 375 mg per day. Also disclosed are dosages of aprocitentan from 325 to 450 mg, or 325 to 375 mg per day. A further preferred dosage range is 360 to 390 mg of aprocitentan per day. According to a more preferred aspect, these dosages of aprocitentan are applied once a day.

The following abbreviations are used throughout the present specification.

ABBREVIATIONS

6MWD 6-minute walk distance
BPA balloon pulmonary angioplasty
CTE chronic thromboembolism
CTEPH chronic thromboembolic pulmonary hypertension
ERA endothelin receptor antagonist
ET endothelin
mPAP mean pulmonary artery pressure
PAH pulmonary arterial hypertension
PAP pulmonary artery pressure
PAWP Pulmonary artery wedge pressure
PDE5 cyclic guanosine 3',5'-monophosphate (cGMP) phosphodiesterase type 5
PEA pulmonary endarterectomy
PH pulmonary hypertension
PVR pulmonary vascular resistance
RAP right arterial pressure (sometimes also referred to as mRAP)
WHO World Health Organization
WHO FC World Health Organization Functional Class

EXPERIMENTAL PART

The following non-limitative examples illustrate the invention.

Examples

Effect of macitentan on decrease in hemoglobin concentration

Hemoglobin measurements were pooled from 3 Phase I clinical studies in healthy volunteers:
Study AC-055-102: Investigation of the PK, PD, safety and tolerability of macitentan in male subjects (the study protocol is described in the following publication: Sidharta et al., Safety, tolerability, pharmacokinetics, and pharmacodynamics of macitentan, an endothelin receptor antagonist, in an ascending multiple-dose study in healthy subjects. *J. Clin. Pharmacol.* (2013), 53(11), 1131-1138)
Study AC-055-116: Investigation of the PK, PD, safety and tolerability of macitentan in male Japanese subjects (the study protocol is described in the following publication: Yokoyama et al., Tolerability, Safety, Pharmacokinetics, and Pharmacodynamics of Macitentan, a New Endothelin Receptor Antagonist, in Healthy Japanese Male Subjects. *Rinsho yakuri/Japanese Journal of Clinical Pharmacology and Therapeutics* (2016), 47, 143-150)
Study AC-055-117: Investigation of the PK, PD, safety and tolerability of macitentan in male Korean subjects (the study protocol is described in the following publication: Ahn et al., Pharmacokinetic-pharmacodynamic relationships of macitentan, a new endothelin receptor antagonist, after multiple dosing in healthy Korean subjects, *Am. J. Cardiovasc. Drugs* (2014), 14(5), 377-385)

Hemoglobin concentrations measured in the morning of Day 11 of macitentan treatment and at baseline on Day −1 were used in the analysis. Changes in hemoglobin concentrations compared to baseline were regressed against the different dose levels of macitentan, including placebo.

An Emax curve with baseline was fitted and the following parameters were estimated by nonlinear regression:
E0: Change in hemoglobin without macitentan
Emax: Maximum change in hemoglobin theoretically could be elicited by macitentan
ED50: the dose resulting in 50% reduction of hemoglobin
The following formula was used:

$$\text{Change in Hemoglobin} = E0 + ((\text{Macitentan Dose} \times E\text{Max})/(\text{Macitentan Dose} + ED50))$$

The resulting dose-response curve is shown in FIG. 1.
Based on the analysis, the maximum effect of macitentan on hemoglobin decrease would be around 1.23 g/dL and the effect of macitentan on hemoglobin decrease plateaus already at the 10 mg dose (see FIG. 1). Therefore, no clinically relevant decrease in hemoglobin is expected above a 10 mg dose of macitentan in humans.

What is claimed is:

1. A method for treating chronic thromboembolic pulmonary hypertension (CTEPH), comprising administering to a human patient in need thereof macitentan at a dosage of 60 mg to 90 mg per day.
2. The method of claim 1, wherein the dosage is 70 mg to 80 mg per day.
3. The method of claim 2, wherein the dosage is 35 mg to 40 mg twice per day.
4. The method of claim 1, wherein the dosage is 75 mg per day.
5. The method of claim 4, wherein the dosage is 37.5 mg twice per day.
6. The method of claim 1, wherein the method reduces a morbidity risk, a mortality risk, or both, of the CTEPH.
7. The method of claim 1, wherein macitentan is administered to the human patient before pulmonary endarterectomy (PEA) surgery.
8. The method of claim 1, wherein the human patient is inoperable with PEA surgery.
9. The method of claim 1, further comprising administering to the patient a PDE5 inhibitor, a prostacyclin analogue, a prostacyclin receptor agonist, or a soluble guanylate cyclase stimulator, or a combination thereof.
10. The method of claim 9, wherein the PDE5 inhibitor is sildenafil, tadalafil, vardenafil, or udenafil; the prostacyclin analogue is epoprostenol, treprostinil, iloprost, or beraprost; the prostacyclin receptor agonist is selexipag or ralinepag; and the soluble guanylate cyclase stimulator is riociguat, olinciguat, praliciguat, or vericiguat.
11. The method of claim 1, further comprising administering to the patient tadalafil, selexipag, or riociguat, or a combination thereof.
12. The method of claim 11, wherein the tadalafil is administered at a dosage of 20 mg to 40 mg per day, the selexipag is administered at a dosage of 0.2 mg to 1.6 mg twice per day, or the riociguat is administered at a dosage of 0.5 mg to 2.5 mg three times per day, or a combination thereof.
13. The method of claim 12, wherein the dosage of tadalafil is 40 mg per day.
14. The method of claim 1, further comprising administering to the patient tadalafil or selexipag, or a combination thereof.
15. The method of claim 1, wherein the patient is already being treated with an endothelin receptor antagonist prior to administering macitentan.
16. The method of claim 15, wherein the endothelin receptor antagonist is bosentan or ambrisentan.
17. The method of claim 1, wherein the human patient suffers from persistent or recurrent pulmonary hypertension (PH) after PEA surgery.
18. The method of claim 1, wherein the human patient has been treated with balloon pulmonary angioplasty (BPA) and PEA surgery prior to administering macitentan.
19. The method of claim 1, wherein the human patient is excluded from BPA.
20. The method of claim 1, wherein the human patient suffers from persistent or recurrent PH after BPA.

* * * * *